United States Patent [19]

Holtkamp, Sr.

[11] Patent Number: Plant 6,431

[45] Date of Patent: Nov. 29, 1988

[54] AFRICAN VIOLET PLANT NAMED AQUARIUS

[76] Inventor: Reinhold Holtkamp, Sr., Werther Strasse 112, D4294 Isselburg, Fed. Rep. of Germany

[21] Appl. No.: 21,740

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Aquarius, characterized by its single violet blue flower; heavily serrated, girl-type leaves; strong, upright flower stems that curve toward the center to form a bouquet above the leaves, profuse flowering, vigorous growth habit, flowering 9–10 weeks after potting, and its long-lasting and non-dropping flowers.

1 Drawing Sheet

1

The present invention comprises a new and distinct cultivar of African violet plant, botanically known as *Saintpaulia ionantha,* and hereinafter referred to by the cultivar name Aquarius.

The new cultivar was referred to during the breeding and selection process by the designation H 50/27, and is a product of a planned breeding program. The new cultivar was originated from a cross made by me in the controlled breeding program in Isselburg, Federal Republic of Germany. The female, or seed parent was a cultivar designated C 81/1 Light Blue. The male, or pollen parent was a cultivar designated XIX 4297 White Girl.

Aquarius was discovered and selected by me in 1982 as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Aquarius has not been observed under all possible environmental conditions. The phenotype may vary significantly with variations in environment such as temperature, light intensity and day length. The following observations, measurements and values describe the new cultivar as grown in a 10 cm pot in Haffen, Federal Republic of Germany and Nashville, Tenn. under greenhouse conditions which closely approximate those generally used in commercial practice.

The following traits have been repeatedly observed and are determined to be basic characteristics of Aquarius which in combination distinguish this African violet as a new and distinct cultivar:

(1) Strong upright flower stems curving toward the center.

(2) Long-lasting, non-dropping, single, solid violet-blue flowers.

(3) Profuse flowering.

(4) Each plant carries 7–8 and more upright flower stems, each of which carries 10–12 flowers.

(5) Vigorous grower.

(6) Plant saleable 9 to 10 weeks after potting.

(7) Seed capsules push through.

2

(8) Very attractive girl-type leaf, indented, strongly serrated with a white to light green center that radiates along the veins.

(9) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight at approximately 1:00 p.m. in Nashville, Tenn.

Botanical classification: *Saintpaulia ionantha,* Ramat., cv. Aquarius.

Parentage:

*Male parent.*—XIX 4297 White Girl.

*Female parent.*—C 81/1 Light Blue.

Propagation: The new cultivar holds its distinguishing characteristics through successive propagations by leaf cuttings.

Plant: From 10 cm to 11 cm tall when grown in pots, and approximately 18–20 cm in diameter when fully grown.

*Leaves.*—General form: round, girl-type, slightly curled up at the center. Diameter: 65–75 mm. Texture: velvety, shiny. Aspect: indentations (especially the younger leaves), strongly serrated, slightly hairy, bright light green center radiating along the veins. Veins: upperside: well visible, light green towards the center; underside: well pronounced, very light green, shiny, occasional, slight purplish touch in between the veins. Color (upper side): yellow green group 147A, center of leaf bright green. Color (under side): yellow green group 148C. Petiole: strong upright, very light green, hairy, purplish at the base.

*Flowers.*—Buds: bell-shaped, 7–8 mm just before opening, light blue. Sepals: five (5). Color: brownish green. Calyx: funnel-shaped. Peduncle: Character: strong, upright, hairy. Color: purplish brown. Individual flowers: Size: 40–45 mm. Shape: single, normal violet shape; 3 large and 2 small petals. Color (upper side): predominantly 90D, center 90B. Color (under side): 90D. Borne: each flower stem carries 10–12 flowers on strong, upright peduncles that curve toward the center. Flowering habit: flowers 9–10 weeks after potting, with a compact flower head standing free above the leaves.

*Reproductive organs.*—Stamens: 2. Anthers: 2 composed of 4 cells. Filaments: green with bluish touch, 5 mm. Pollen color: yellow group 7A. Styles: 7 mm, bluish, with a light green, hairy base of ovary.

*Roots.*—Normally developed, white when young turning slightly brownish when older.

Disease resistance: Good.

General observations: Aquarius has a very attractive appearance due to its bright green strongly serrated leaves with a light green center. A tight bouquet of flowers on relatively long stems, free-standing above the leaves, is composed of solid violet-blue flowers contrasting with the bright yellow anthers. Occasionally, 1 or 2 additional very small petals develop over the 2 smaller petals. The flowers are long-lasting and non-dropping.

I claim:

1. A new and distinct cultivar of African violet named Aquarius, as described and illustrated, and particularly characterized by its single violet blue flower; heavily serrated, girl-type leaves; strong, upright flower stems that curve toward the center to form a bouquet above the leaves, profuse flowering, vigorous growth habit, flowering 9–10 weeks after potting, and its long-lasting and non-dropping flowers.

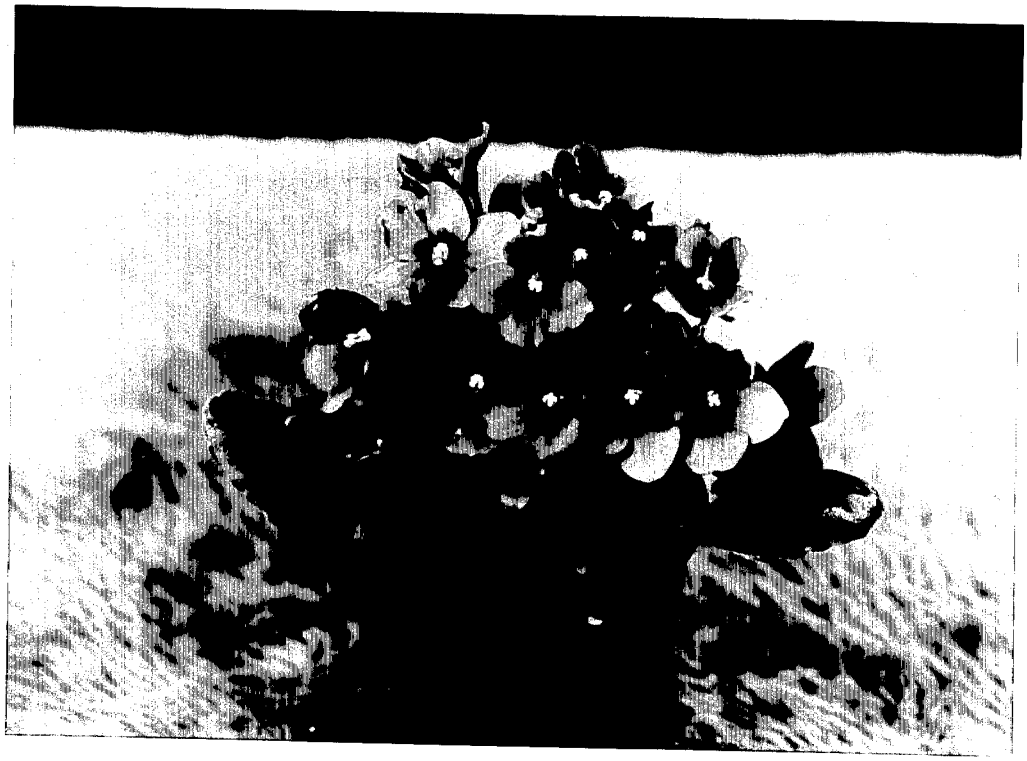

* * * * *